United States Patent
Carlson, II

[11] Patent Number: 5,549,868
[45] Date of Patent: Aug. 27, 1996

[54] METHOD OF STERILIZING AN ARTICLE

[75] Inventor: Gerald I. Carlson, II, Marietta, Ga.

[73] Assignee: Kimberly-Clark Corporation, Neenah, Wis.

[21] Appl. No.: 426,338

[22] Filed: Apr. 21, 1995

[51] Int. Cl.$^6$ .................. B01J 19/00; A61L 2/08
[52] U.S. Cl. .................. 422/1.000; 422/26; 422/28; 422/40; 422/302
[58] Field of Search .................. 422/26, 28, 29, 422/40, 292, 1, 300, 302; 206/438–440, 363, 370; 428/212

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,612,803 | 10/1971 | Klaas | 219/10.53 |
| 3,645,768 | 2/1972 | Coco et al. | |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,855,046 | 12/1974 | Hansen et al. | 161/150 |
| 3,909,009 | 9/1975 | Cvetko et al. | 274/37 |
| 4,041,203 | 8/1977 | Brock et al. | 428/157 |
| 4,307,143 | 12/1981 | Meitner | 252/91 |
| 4,340,563 | 7/1982 | Appel et al. | 264/518 |
| 4,374,888 | 2/1983 | Bornslaeger | 428/198 |
| 4,644,586 | 2/1987 | Padgett | 422/26 X |
| 4,707,398 | 11/1987 | Boggs | 428/224 |
| 4,751,133 | 6/1988 | Szycher et al. | 428/254 |
| 4,902,478 | 2/1990 | Hambleton | 206/439 X |
| 5,165,539 | 11/1992 | Weber et al. | 206/363 |
| 5,165,979 | 11/1992 | Watkins et al. | 428/113 |
| 5,169,706 | 12/1992 | Collier, IV et al. | 428/152 |
| 5,180,632 | 1/1993 | Edenbaum et al. | 428/255 |
| 5,188,885 | 2/1993 | Timmons et al. | 428/284 |
| 5,204,174 | 4/1993 | Daponte et al. | 428/286 |
| 5,344,017 | 9/1994 | Wittrock | 206/363 X |
| 5,378,531 | 1/1995 | Larson et al. | 428/255 |

OTHER PUBLICATIONS

Jezic et al., Research Disclosure, "Re–Sealable and Radiation–Sterilizable Packaging," Apr. 1988.

*Primary Examiner*—Robert Warden
*Assistant Examiner*—Krisanne M. Thornton
*Attorney, Agent, or Firm*—David J. Alexander

[57] ABSTRACT

A process for forming sterilization wrap and sterilizing an article, such as an surgical instrument tray, wrapped with said sterilization wrap is provided. The sterilization wrap is formed by securing a sterilization reactive material to the sterilization wrap. The article to be sterilized may be wrapped with the sterilization wrap of the present invention such that the sterilization reactive material is positioned between a portion of the sterilization wrap overlying a weight bearing surface of the instrument tray and an instrument tray receiving surface, such as a table or storage shelf. Upon exposure to sterilization conditions for a sufficient time, the sterilization reactive material may stiffen, thicken, become less porous, less dense or any combination thereof.

21 Claims, 1 Drawing Sheet

METHOD OF STERILIZING AN ARTICLE

FIELD OF THE INVENTION

The present invention relates to liquid and particulate barrier fabrics. More particularly, the present invention relates to liquid and particulate barrier fabrics suitable for use as sterilization wrap.

BACKGROUND OF THE INVENTION

While a number of hospital and operating room supplies today are disposable most hospitals still reuse many supplies, including instruments used in surgery. Such instruments typically include such things as clamps, scalpel blade handles, retractors, forceps, scissors, towels, basins and the like. However, before operating room supplies can be reused, they must be sterilized.

The process of sterilizing these supplies typically involves collecting the non-sterile supplies and placing them in an instrument tray. The instrument tray may be formed from stainless steel and have an open top and a perforated bottom panel. The instrument tray is then wrapped with generally two sheets of material. Each sheet of material is desirably a sheet of sterilization wrap.

A suitable sterilization wrap will allow entry and exit of a sterilant into and out of the instrument tray, while prohibiting the entry of bacteria or other contaminates into the instrument tray. Examples of suitable sterilization wraps include KIMGUARD® Sterile-Wrap, KIMGUARD ONE-STEP™ Sterile-Wrap and SPUNGUARD® Sterilization Wrap, which are manufactured and sold by Kimberly Clark Corporation. These sterilization wraps are generally formed from a spunbond/meltblown/spunbond laminate which is available in a variety of basis weights. Examples of suitable sterilants include steam, ethylene oxide and plasma.

Once the instruments have been sterilized, the wrapped instrument tray, containing the sterilized supplies, may be transported directly to a point of use. Alternatively, the sterilized wrapped instrument tray, containing the sterilized supplies, may be stored. In this way, the supplies are kept within the sterile confines of the wrapped instrument tray until just prior to their use.

During transportation to either the point of use or storage, the wrapped instrument tray may be handled several times. Each time the wrapped instrument tray is handled there is the potential that the sterility of the instrument tray and its contents may be compromised. The sterility of the wrapped instrument tray and its contents becomes compromised when a tear or other breach in the sterilization wrap occurs or when the sterilization wrap becomes wet or when liquid penetrates the sterilization wrap. If the sterility of the wrapped instrument tray is compromised at any time prior to the use of the supplies within the instrument tray, the supplies are considered contaminated and unusable until the instrument tray containing the supplies is rewrapped with sterilization wrap and re-sterilized.

In an effort to avoid tearing or otherwise breaching the sterilization wrap material, the storage shelves which contact the bottom of the wrapped instrument tray have been padded or cushioned. Examples of materials used for such cushioning or padding include foam or linen materials. Cushioning or padding, it is thought, reduces the risk of cuts, holes and tears in the sterilization wrap by reducing the amount of shear the sterilization wrap experiences when a wrapped instrument tray is pulled or dragged across the storage shelf.

Another effort to avoid tearing or otherwise breaching the sterilization wrap material includes the use of the surgical instrument transport tray described in U.S. Pat. No. 5,165,539 assigned to Kimberly-Clark Corporation. When this surgical instrument transport tray is used, the bottom of the transport tray accepts the shearing motion and frictional forces generated by the tray moving across the storage shelf thereby avoiding damage to the sterilization wrap.

Thus, while the above efforts have meet with varying degrees of success, there remains a need for other alternatives which avoid compromising the sterility of the instrument tray and its contents.

SUMMARY OF THE INVENTION

The present invention provides a sterilization wrap which includes at least one layer and a sterilization reactive material secured to the layer. Desirably, the sterilization reactive material is positioned between a weight bearing surface of an instrument tray and an instrument tray receiving surface. More desirably, the sterilization reactive material is positioned between a portion of at least one layer, such as a sterilization wrap layer, overlying and in contact with a weight bearing surface of the instrument tray and an instrument tray receiving surface. In this way, upon exposure to sterilization conditions, the shear forces and/or other breaching forces experienced by the layer are dissipated or reduced by the reacted sterilization reactive material. Upon exposure to sterilization conditions for a sufficient time, the sterilization reactive material may stiffen, thicken, become less porous, less dense or any combination thereof.

In one embodiment, the sterilization reactive material may be secured to the layer by capture of the sterilization reactive material between the layer and another material layer. In another embodiment, the sterilization reactive material may be secured to the layer by gluing or fusing. In still another embodiment, the sterilization reactive material may be coated on the layer or portions thereof. Such coating may be accomplished by dipping or spraying the sterilization reactive material onto a surface of the layer.

The layer is desirably formed from a sterilization wrap material. The sterilization wrap material, such as a sterilization wrap fabric, may be formed from natural or synthetic materials. Examples of natural materials include cotton, wool or cellulose. Examples of synthetic materials include synthetic polymers and particularly, polyolefin polymers. In one embodiment, the sterilization wrap material may be formed from a nonwoven laminate and more particularly a spunbond/meltblown/spunbond laminate.

DETAILED DESCRIPTION OF THE INVENTION

Figure 1:
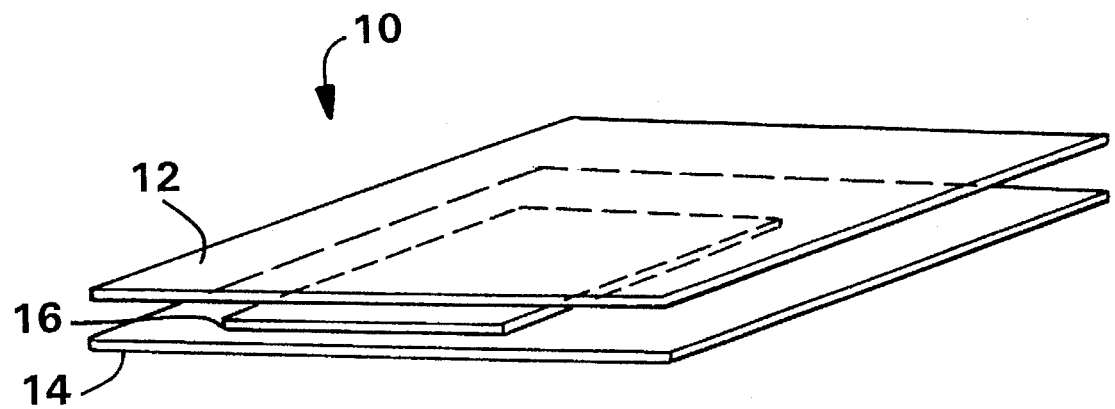
FIG. 1 is an exploded, perspective view of the sterilization wrap of the present invention illustrating a layer of sterilization reactive material between two layers.

As used herein, the term "sterilization reactive material" refers to any material or a combination of materials which, upon sufficient exposure to sterilization conditions, undergoes a change in its physical state or chemical state or both. Desirably, such change in the sterilization reactive material between pre- and post- exposure to sterilization conditions may include, for example, the post exposure material being stiffer than the pre exposure material, the post exposure material being thicker than the pre exposure material, the post exposure material being less porous than the pre exposure material, the post exposure material being more dense than the pre exposure material, and any combination thereof. Any other change which further enhances the sterile wrap materials ability to maintain the sterile conditions is also envisioned.

An example of a sterilization reactive material is polystyrene in combination with a blowing agent. A blowing agent is generally a gas or a material capable of producing a gas, which is incorporated into a polymer melt where the blowing agent becomes trapped. In the case of a chemical blowing agent, the gas is produced in situ either by the chemical decomposition, often by heat, of the blowing agent, or by gas production from another type chemical reaction, as in the reaction of water with isocyanates to produce carbon dioxide in polyurethane foam formation.

In the pre-exposure to a sterilization condition state, polystyrene in combination with a blowing agent may be in granular or sheet form. When the polystyrene/blowing agent is exposed to sufficient temperature, generally between the range of about 250° F. to about 290° F., the polystyrene/blowing agent expands and stiffens.

As used herein, the term "sterilization conditions" refers to those parameters unique to a sterilization process which, when non-sterile supplies wrapped in sterilization wrap are exposed thereto for a sufficient time, sterilize such non-sterile supplies. Examples of such parameters include, a particular temperature or temperature range, a particular humidity value or humidity range, a pressure or a pressure range, and sterilants, such as steam, ethylene oxide, and plasma. Examples of sterilization processes include steam sterilization, ethylene oxide sterilization, and plasma sterilization.

As used herein, the term "nonwoven web" refers to a web that has a structure of individual fibers or filaments which are interlaid, but not in an identifiable repeating manner.

As used herein the term "spunbond fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al which are all herein incorporated by reference.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Meltblowing is described, for example, in U.S. Pat. No. 3,849,241 to Buntin, U.S. Pat. No. 4,307,143 to Meitner et al., and U.S. Pat. No. 4,707,398 to Wisneski et al which are all herein incorporated by reference.

Referring to FIG. 1, the sterilization wrap of the present invention is generally designated by the reference number 10. The sterilization wrap 10 includes a first layer 12 in juxtaposition with a second layer 14. Between the first layer 12 and the second layer 14 is a layer 16 of sterilization reactive material. In one embodiment, illustrated in FIGS. 2 and 3, the sterilization reactive material layer 16 may be secured to the sterilization wrap 10 by positioning the sterilization reactive material 16 between layers 12 and 14. In another embodiment, the sterilization reactive material layer 16 may be secured to either layer 12 or 14 by gluing or fusing the sterilization reactive material thereto. In still another embodiment, the sterilization reactive material layer 16 may be coated on either layer 12 or 14 or portions thereof. Such coating may be accomplished by dipping or spraying the sterilization reactive material onto a surface of either layer 12 or 14.

The first layer 12 is desirably a porous layer and may be formed from a woven or nonwoven web. More desirably, the first layer 12 may be formed from a sterilization wrap material, such as a sterilization wrap fabric. Generally, a sterilization wrap material, when wrapped around the tray or package in a certain prescribed manner and exposed to sterilization conditions, will permit the entry of sterilizing vapor/gas or other medium to sterilize the contents of the tray while denying the ingress of contaminants such as bacteria and other infectious causing materials after sterilization. In many instances the instrument tray is wrapped with two sheets of sterilization wrap material.

The first layer 12 may be a single sheet formed from a single layer or multiple layers. Generally, when multiple layers are bonded together, as described in greater detail below, the bonded multiple layers are referred to as a "laminate". Alternatively, the first layer 12 may be formed from multiple sheets. These multiple sheets may include at least one sheet formed from a single layer, at least one sheet formed from multiple layers, at least one sheet formed from a laminate, and more particularly, a laminate wherein the multiple layers have been sufficiently bonded together so as to form a unitary structure as defined in U.S. Pat. No. 4,041,203 to Brock et al., or a combination thereof. An example of a single sheet, multi-layered laminate sterilization wrap is the spunbond/meltblown/spunbond laminate or "SMS" nonwoven web laminate described in greater detail below.

The second layer 14 may be formed from material similar to the material used to form the first layer 12, provided at least one of the layers, 12 or 14 is formed from sterile wrap material. When the first layer 12 is formed from sterilization wrap fabric, the second layer 14 may be formed from material suitable for securing the sterilization reactive material 16 to the first layer 12. Furthermore, the dimensions of the second layer 14 may be smaller than the dimensions of the first layer 12, and more particularly, the second layer 14 may be sufficiently sized to overly the sterilization reactive material 16 and a portion of the first layer 12. In this way, the portions of the second layer 14 overlying portions of the first layer 12 may be secured to the first layer 12 by gluing, stitching, heat sealing, bonding or other methods well known to those skilled in the art.

Thermoplastic polymers are well suited for the formation of nonwoven materials, and particularly nonwoven webs, which are useful for forming either the first layer 12 or the second layer 14. Nonwoven materials can be made from a variety of processes including, but not limited to, air laying processes, wet laid processes, hydroentangling processes, spunbonding, meltblowing, staple fiber carding and bonding, and solution spinning.

The fibers or filaments used in forming nonwoven webs may be homo-polymeric, co-polymeric, bi- or multi-component polymeric or polymer blends. In one embodiment, these fibers may further be formed through appropriate processes such that they are spiral-shaped. When the fibers are bi- or multi-component, one of the components may be homo-polymeric, co-polymeric, or a polymer blend. The orientation of individual components, such as a first and a second component, may be sheath-core or side-by-side.

By way of example only, thermoplastic polymers may include, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as poly(ethyl acrylate), poly(methyl methacrylate), and the like; fluorocarbon polymers, such as perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxy-1,4-phenylenesulfonyl-4,4'-biphenylene), and the like; polycarbonates, such as poly(bisphenol A) or poly(carbonyldioxy-1,4-phenyleneisopropylidene-1,4-phenylene), and the like; polyesters, such as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; copolymers of the foregoing, such as a polypropylene-ethylene, polypropylene-polyethylene, polyethylene-polyvinyl alcohol, acrylonitrile-butadiene-styrene (ABS) copolymers, and the like.

In one embodiment, the first layer 12 may be formed from a multi-layered nonwoven laminate. The multi-layered nonwoven laminate includes at least one layer formed from meltblown fibers which is positioned between two layers formed from spunbond fibers, such as a spunbond/meltblown/spunbond (SMS) nonwoven web laminate. Examples of nonwoven web laminates are disclosed in U.S. Pat. No. 4,041,203 to Brock et al., U.S. Pat. No. 5,169,706 to Collier, et al, and U.S. Pat. No. 4,374,888 to Bornslaeger which are all herein incorporated by reference.

More particularly, the spunbond fibers may be formed from polypropylene. Suitable polypropylenes for the spunbond layers are commercially available as PD-9355 from the Exxon Chemical Company of Baytown, Tex.

The meltblown fibers may also be formed from polyolefin polymers, and more particularly, a blend of polypropylene and polybutylene. Examples of such meltblown fibers are contained in U.S. Pat. Nos. 5,165,979 and 5,204,174 which are incorporated herein by reference.

Nonwoven webs can be made from a variety of processes including, but not limited to, air laying processes, wet laid processes, hydroentangling processes, spunbonding, meltblowing, staple fiber carding and bonding, and solution spinning. In one embodiment, the SMS nonwoven web laminate may be made by sequentially depositing onto a moving forming belt first a spunbond fabric layer, then a meltblown fabric layer and last another spunbond layer and then bonding the layers together in a manner described below. Alternatively, the layers may be made individually, collected in rolls, and combined in a separate bonding step. Such SMS nonwoven web laminates usually have a basis weight of from about 0.1 to 12 ounces per square yard (osy) (3 to 400 grams per square meter (gsm)), or more particularly from about 0.75 to about 5 osy (25 to 170 gsm) and still more particularly from about 0.75 to about 3 osy (25 to 100 gsm).

Nonwoven webs may be generally bonded together to form a laminate in some manner as they are produced in order to give them sufficient structural integrity to withstand the rigors of further processing into a finished product. Bonding can be accomplished in a number of ways such as hydroentanglement, needling, ultrasonic bonding, adhesive bonding and thermal bonding.

Ultrasonic bonding is performed, for example, by passing the nonwoven webs between a sonic horn and anvil roll as illustrated in U.S. Pat. No. 4,374,888 to Bornslaeger. Thermal bonding of a nonwoven webs may be accomplished by passing the same between the rolls of a calendering machine. At least one of the rollers of the calender is heated and at least one of the rollers, not necessarily the same one as the heated one, has a pattern which is imprinted upon the nonwoven webs as they pass between the rollers. As the webs pass between the rollers, the webs are subjected to pressure as well as heat. The combination of heat and pressure applied in a particular pattern results in the creation of fused bond areas in the nonwoven webs where the bonds thereon correspond to the pattern of bond points on the calender roll.

Various patterns for calender rolls have been developed. One example is the Hansen-Pennings pattern with between about 10 to 25% bond area with about 100 to 500 bonds/square inch as taught in U.S. Pat. No. 3,855,046 to Hansen and Pennings. Another common pattern is a diamond pattern with repeating and slightly offset diamonds.

The exact calender temperature and pressure for bonding the nonwoven webs to form a nonwoven web laminate depend on the thermoplastic(s) from which the nonwoven web is made. Generally for nonwoven webs formed from polyolefins, preferred temperatures are between 150 and 350° F. (66 and 177° C.) and the pressure is between 300 and 1000 pounds per lineal inch. More particularly, for polypropylene, the preferred temperatures are between 270 and 320° F. (132 and 160° C.) and the pressure is between 400 and 800 pounds per lineal inch.

In those instances where the nonwoven web is used in or around flammable materials and static discharge is a concern, the nonwoven web may be treated with any number of antistatic materials. In these instances, the antistatic material may be applied to the nonwoven by any number of techniques including, but not limited to dipping the nonwoven into a solution containing the antistatic material or by spraying the nonwoven with a solution containing the antistatic material. In some instances the antistatic material may be applied to both the external surfaces of the nonwoven and/or the bulk of the nonwoven. In other instances, the antistatic material may be applied to portions of the nonwoven, such as a selected surface or surfaces thereof. Of particular usefulness is the antistat or antistatic material known as ZELEC®, an alcohol phosphate salt product of the Du Pont Corporation. The nonwoven web may be treated with the antistatic material either before or after subjecting the web to charging. Furthermore, some or all of the material layers may be treated with the antistatic material. In those instances where only some of the material layers are treated with antistatic material, the non-treated layer or layers may be subjected to charging prior to or after combining with the antistatic treated layer or layers.

Additionally, in those instances where the nonwoven web is used around alcohol, the nonwoven web may be treated with an alcohol repellent material. In these instances, the alcohol repellent material may be applied to the nonwoven by any number of techniques including, but not limited to dipping or by spraying the nonwoven web with a solution containing the alcohol repellent material. In some instances the alcohol repellent material may be applied to both the external surfaces of the nonwoven and the bulk of the nonwoven. In other instances, the alcohol repellent material may be applied to portions of the nonwoven, such as a selected surface or surfaces thereof.

The sterilization wrap of this invention may also contain fire retardants for increased resistance to fire, pigments, and/or chemicals such as hindered amines to provide enhanced ultraviolet light resistance. Fire retardants and pigments for spunbond and meltblown thermoplastic polymers are known in the art. A pigment, if used, is generally present in an amount less than 5 weight percent of the layer.

Figure 2:
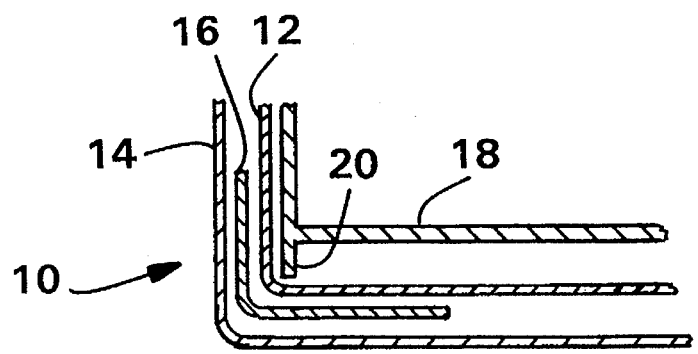
FIG. 2 is a fragmented cross-sectional view of an embodiment of the present invention overlying a portion of a surgical instrument tray.

Referring now to FIG. 2, a portion of the sterilization wrap 10 is overlying a portion of the bottom of an instrument tray 18 having a shoulder 20. The sterilization reactive material 16 is positioned between the first and second layers 12 and 14.

Desirably, prior to exposure to sterilization conditions, the sterilization reactive materials are sufficiently pliable and/or conformable. In this way, as illustrated in FIG. 2, the sterilization reactive material 16 may conform to the shape of an article or portion thereof, such as the instrument tray 18, when such article is wrapped with the sterilization wrap 10.

Figure 3:
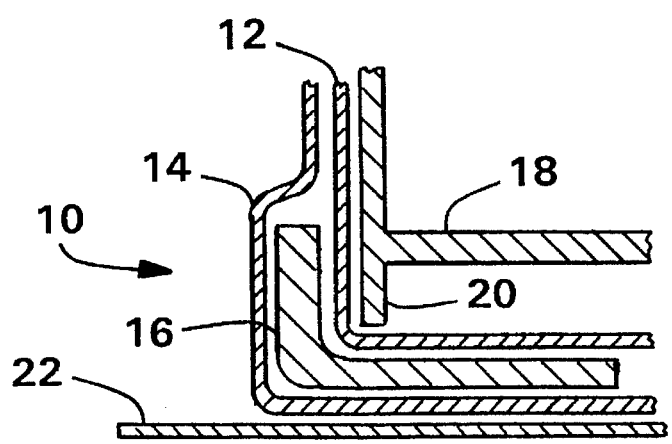
FIG. 3, is a fragmented cross-sectional view of another embodiment of the present invention overlying a portion of a surgical instrument tray.

FIG. 3 is similar to FIG. 2 with the exception that the sterilization reactive material 16 is illustrated in a reacted, expanded state with the outer layer 14 being sufficiently expandable to conform to the reacted, expanded state of the sterilization reactive material 16.

With continued reference to FIG. 3, the sterilization reactive material 16 is desirably positioned between one or more weight bearing surfaces of the instrument tray 18, such as the shoulder 20 and an instrument tray receiving surface 22. More desirably, the sterilization reactive material 16 is positioned between a portion of at least one sheet of sterilization wrap (layer 12) overlying said weight bearing surface of the instrument tray 18 and the instrument tray receiving surface 22. Most desirably, the sterilization reactive material 16 is positioned between a portion of at least two juxtaposed sheets of sterilization wrap (layer 12) which overly a weight bearing surface of the instrument tray 18 and the instrument tray receiving surface 22. The instrument tray receiving surfaces 22 may be, for example, a table top, a storage shelf or a guide channel.

In operation, the instrument tray 18 containing non-sterile supplies is wrapped with the sterilization wrap 10 and placed in a sterilizer, such as a steam sterilizer, ethylene oxide sterilizer or a plasma sterilizer. The instrument tray 18 is wrapped with the sterilization wrap 10 such that the unreacted sterilization reactive material 16 is positioned between one or more weight bearing surfaces of the instrument tray 18 and the instrument tray receiving surface.

Upon exposure to the sterilization conditions produced by the sterilizer, the sterilization reactive material 16 reacts as previously described. In this way, the shear forces and/or other sterilization wrap breaching forces experienced by the portion of the sterilization wrap 10 captured between the sterilization reactive material 16 and the instrument tray 18 are dissipated or reduced by the reacted sterilization reactive material 16. These forces are reduced or dissipated by the reacted sterilization reactive material 16 because, for example, in the most desired embodiment, the reacted sterilization reactive material 16, and not the sterilization wrap layer 12, initially contacts the instrument tray receiving surface 22. In other words, these forces, such as frictional and shear forces, generated by the movement of the wrapped instrument tray 18 onto and/or across the instrument tray receiving surface 22 are initially encountered by the reacted sterilization reactive material 16 and not the sterilization wrap layer 12.

In instances where the sterilization reactive material 16 is positioned between two layers of sterilization wrap, 12 and 14, the reacted sterilization reactive material 16 may be sufficiently compressible so as to dissipate these forces such that the outer sterilization wrap layer 14 is not breached by such forces. Furthermore, in this configuration, in the event a tear or other such breach were to occur in a portion of the outer sterilization wrap layer 14 overlying the reacted sterilization reacted material 16, the reacted sterilization reactive material 16 may be sufficiently impermeable to prevent bacterial or other contaminate intrusion.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. A process for sterilizing an instrument tray comprising the steps of:

securing a sterilization reactive material to a sheet of sterilization wrap;

wrapping the instrument tray with the sheet of sterilization wrap such that the sterilization reactive material is positioned between a weight bearing surface of the instrument tray and an instrument tray receiving surface; and exposing the product of the preceding step to sterilization conditions.

2. The process of claim 1 wherein the sheet of sterilization wrap comprised a spunbond/meltblown/spunbond nonwoven web laminate.

3. The process of claim 1 wherein the sterilization reactive material comprises polystyrene.

4. The process of claim 1 wherein the sterilization conditions are further defined as steam sterilization conditions.

5. A process for sterilizing an instrument tray comprising the steps of:

overlying one sheet of sterilization wrap with another sheet of sterilization wrap;

securing a sterilization reactive material to one of the sheets of sterilization wrap;

wrapping the instrument tray with the product of the preceding step such that the sterilization reactive material is positioned between a weight bearing surface of the instrument tray and an instrument tray receiving surface; and exposing the product of the preceding step to sterilization conditions.

6. The process of claim 5 wherein the sterilization reactive material comprises polystyrene.

7. The process of claim 5 wherein each sheet of sterilization wrap is formed from a nonwoven web.

8. The process of claim 7 wherein each nonwoven web is formed from a spunbond/meltblown/spunbond laminate.

9. The process of claim 5 wherein the step of securing is further defined by securing the sterilization reactive material to one of the sheets sterilization wrap such that the sterilization reactive material is positioned between the sheets of sterilization wrap.

10. The process of claim 1 wherein after the exposing step, the sterilization reactive material is stiffer than before the exposing step.

11. The process of claim 1 wherein after the exposing step, the sterilization reactive material is thicker than before the exposing step.

12. The process of claim 1 wherein after the exposing step, the sterilization reactive material is less porous than before the exposing step.

13. The process of claim 5 wherein after the exposing step, the sterilization reactive material is stiffer than before the exposing step.

14. The process of claim 5 wherein after the exposing step, the sterilization reactive material is thicker than before the exposing step.

15. The process of claim 5 wherein after the exposing step, the sterilization reactive material is less porous than before the exposing step.

16. A process for sterilizing an instrument tray comprising the steps of:

securing a sterilization reactive material to a sheet of sterilization wrap;

wrapping the instrument tray with the sheet of sterilization wrap such that the sterilization reactive material is positioned between a weight bearing surface of the instrument tray and an instrument tray receiving surface; and exposing the product of the preceding step to sterilization conditions which include a temperature range of about 250° F. to about 290° F.

17. The process of claim 16 wherein the sheet of sterilization wrap comprises a nonwoven web.

18. The process of claim 17 wherein the nonwoven web comprises a spunbond/meltblown/spunbond laminate.

19. The process of claim 16 wherein after the exposing step, the sterilization reactive material is stiffer than before the exposing step.

20. The process of claim 16 wherein after the exposing step, the sterilization reactive material is thicker than before the exposing step.

21. The process of claim 16 wherein after the exposing step, the sterilization reactive material is less porous than before the exposing step.

\* \* \* \* \*